United States Patent [19]

Helfer et al.

[11] 4,290,425

[45] Sep. 22, 1981

[54] INFANT SUPPORT BOARD

[75] Inventors: Joel N. Helfer, New Haven; Elisa M. Ferrara, Hartford, both of Conn.

[73] Assignee: American Home Products Corporation, New York, N.Y.

[21] Appl. No.: 99,168

[22] Filed: Nov. 30, 1979

[51] Int. Cl.³ .............................................. A61F 13/00
[52] U.S. Cl. .................................. 128/133; 128/89 R
[58] Field of Search .................. 128/133, 87 R, 89 R, 128/DIG. 6, 134

[56] References Cited

U.S. PATENT DOCUMENTS

| 2,606,554 | 8/1952 | Simon | 128/133 |
| 2,763,264 | 9/1956 | McInnerny | 128/133 |
| 3,232,289 | 2/1966 | Zimmerman | 128/87 R |
| 3,779,550 | 12/1973 | Benoun | 128/89 R X |
| 3,850,167 | 11/1974 | Seeley | 128/89 R |
| 3,938,509 | 2/1976 | Barber | 128/89 R |
| 3,942,522 | 3/1976 | Wilson | 128/89 R |

Primary Examiner—John D. Yasko
Attorney, Agent, or Firm—Eugene L. Flanagan, III

[57] ABSTRACT

A support board for use in securing the extremities of an infant against motion and method of assembling same. A rigid support member is provided. A pad of flexible material is shaped to back the support member and form a plurality of flexible straps for holding the support board to the extremity. In a preferred method of assembling the support board, the pad is affixed to the support member by folding a central member of the pad over two sides of the support member and affixing the support member between the folds of the central member.

7 Claims, 4 Drawing Figures

INFANT SUPPORT BOARD

BACKGROUND

The present invention relates to support boards for use in securing the extremities of an infant against motion, for example in protecting the infant against injury while infusing intravenous fluids.

To infuse fluids in the veins of an infant, a butterfly needle is placed in a vein of the infant through the skin of an arm, hand, foot or leg and is left in place to communicate fluids to the vein. While the needle is thus in place in one of the infant's extremities, that extremity must be secured against motion to prevent dislodgement of the needle and injury to the infant.

Nurses practicing in the neonatal area have developed makeshift devices for securing the infant's extremity to the bed sheets. For example, a portion of a diaper or a piece of gauze is taped around a tongue blade and taped to the extremity, the diaper or gauze then being clipped to the bed sheet to prevent motion. Vinyl has also been used for this purpose in place of the diaper or gauze material.

The correct practice is to back the tape with a second piece of tape so that the adhesive surface will not contact the infant's skin. This prevents stripping of the skin from the extremity when the tape is removed. In practice however, backing has not always been used since this is time consuming. The resultant breakdown of the skin leaves the irritated site subject to infection.

In neonatal applications, the child is placed in an incubator or beneath a radiant warmer. The use of tape to secure the device to the infant is not advisable under these circumstances since the tape can melt, becoming fused to the skin and causing skin breakdown, which also increases the likelihood of infection.

Available materials which overcome the disadvantages of tape for use in holding an arm board against the arm of a patient include a fabric laminate sold under the trademark Velfoam. This material includes a napped fabric laminated with a foam material to affix the board to the patient's arm; strips of this material are wound about the board and the arm, and held together with hook tape. However, this method does not insure that the arm board will not be moveable relative to the patient's arm. This problem is particularly acute in neonatal applications where the support board is necessarily small and the child is prone to frequent, random movements. Also, this method is not well adapted for affixing a support to the infant's foot and leg since the board is disposed at an angle thereto.

SUMMARY

A support board for use in securing the extremities of an infant against motion is provided. A rigid support member is affixed to the extremity by a pad of flexible material shaped to back the support member and form a plurality of flexible straps for holding the support board to the extremity. Since the straps are integral with the backing of the support member, the support board will remain secured to the infant's extremity despite its movements. Since the straps are flexible, they can be wound about the limbs even though they are angled to the board. Moreover, the device is easy to apply, not requiring the use of backed tape or other time consuming methods. Thus, the risk that busy medical personnel will avoid such methods as an expedient is substantially reduced.

In a preferred embodiment of the invention, the pad of flexible material is folded over the support member so that on one side it is adapted to contact the infant's skin and on the other as folded it can be affixed to bed sheets and the like, for example with a safety pin.

A method is provided for assembling a support board for use in securing the extremities of an infant against motion. A rigid support member is provided along with a pad of flexible material having a central member and straps integral with the central member. The central member of the pad is then affixed to the support member. In a preferred method of assembly, the central member of the pad is affixed to the support member by folding the central member over two sides of the support member and affixing the support member between the folds of the central member.

DESCRIPTION OF PREFERRED EMBODIMENTS

Figure 1:
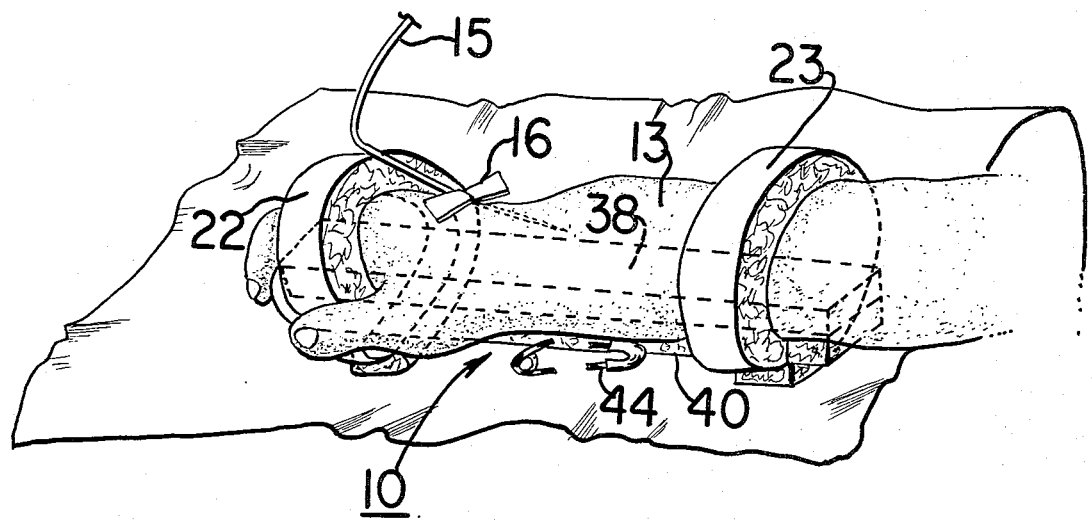
FIG. 1 illustrates a first embodiment of the invention in use for securing an infant's forearm and hand to a bed sheet while a needle is in place to infuse fluids in a vein.

FIG. 1 illustrates generally at 10, one embodiment of the present invention in use in securing an infant's arm 13 against motion while fluids are infused intravenously through a tube 15 connected to a butterfly needle 16 applied to the back of the infant's hand.

Figure 2:
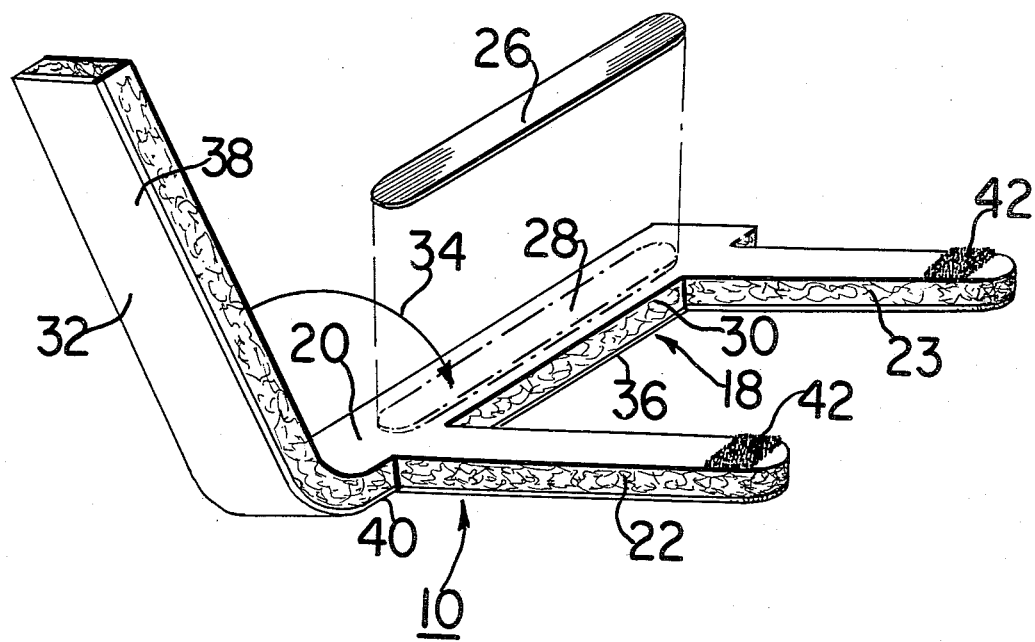
FIG. 2 is an isometric, exploded view of the first embodiment of the invention as shown in use in FIG. 1.

With particular reference to FIG. 2, the first embodiment of the present invention is assembled from a pad 18 having a central member 20 and first and second straps 22 and 23 integral with central member 20 and formed transverse to the longitudinal axis of central member 20, and a rigid support member 26. Pad 18 is cut from a single piece of fabric-foam laminate, such as a material sold under the trademark Velfoam. Rigid support member 26 is made of wood, plastic or other suitable material and has an elongated flat shape with rounded ends.

Support member 26 is affixed to a first portion 28 of central member 20 on the surface of the relatively thick foam layer 30 by an adhesive or other suitable means. A second portion 32 of central member 20 arranged longitudinally with first portion 28 is folded over rigid support member 26 in the direction shown by arrow 34 so that the surface of the foam layer of portion 32 is in contact with rigid support member 26 and is affixed thereto and to first portion 28 by heating, ultrasonic welding or an adhesive such that the fabric layer 36 of pad 18 forms a first outer side 38 and a second outer side 40. Portion 32 can also be formed along the long edge of first portion 28. Accordingly, central member 20, as folded and affixed to itself retains support member 26 therebetween.

First and second straps 22 and 23 are arranged in spaced relation on one side of first portion 28 of central member 20. On the ends of straps 22 and 23 opposite first portion 28 respective fabric hooks 42 are arranged on the foam side. With reference to FIG. 1, the first embodiment 10 as assembled is applied to the infant's arm 13 by placing the arm longitudinally on first outer side 38 such that the palm of the hand grasps the folded end of central member 20. Strap 22 is wound over the fingers with the exception of the thumb and is affixed to second outer side 40 of central member 20 by means of the fabric hook 42; second strap 23 is wound around the forearm and affixed to outer side 40 by means of its respective fabric hook 42. The second outer side 40 is then clipped to the bed sheet, for example by means of a safety pin 44. In the alternative, the safety pin may be clipped through both of portions 28 and 32 and through the bed sheet.

Figure 3:
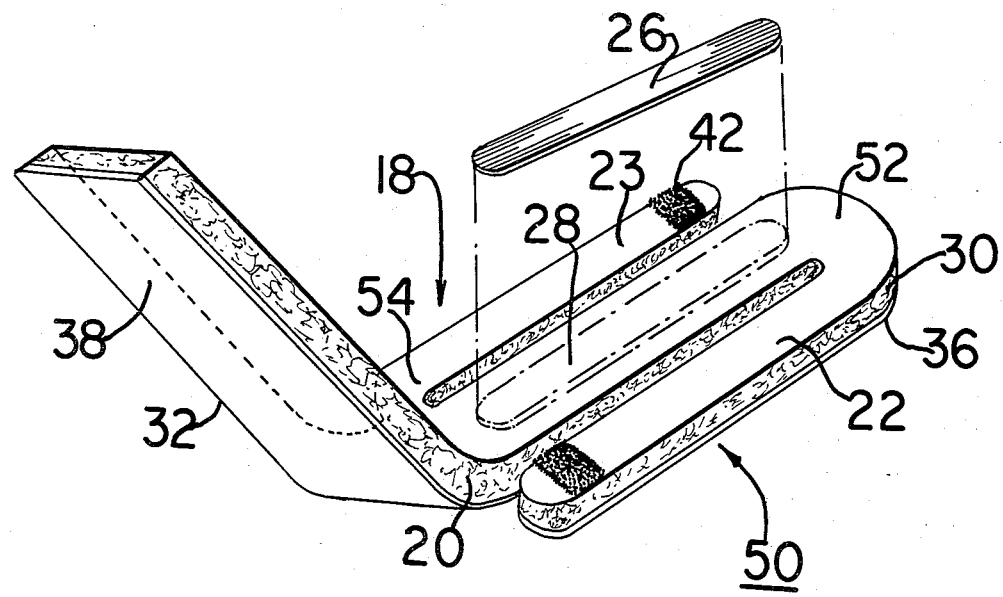
FIG. 3 is an isometric, exploded view of a second embodiment of the invention.

A second embodiment 50 of the invention is shown in exploded form in FIG. 3. Elements of second embodiment 50 corresponding to those of first embodiment 10 are designated by the same reference numerals. In embodiment 50, straps 22 and 23 are arranged parallel to first portion 28 of central member 20 on opposite sides thereof. Strap 22 is connected to first portion 28 by means of a curved connecting section 52 attached to first portion 28 on the side opposite second portion 32. Second strap 23 is connected to first portion 28 through a second curved connecting section 54 attached to first portion 28 adjacent second portion 32.

The second embodiment 50 is assembled in the same fashion as first embodiment 10 of FIG. 2. Rigid support member 26 is affixed longitudinally to the foam side of first portion 28. Thereafter second portion 32 is folded over rigid support member 26 and is affixed thereto and to first portion 28.

Figure 4:
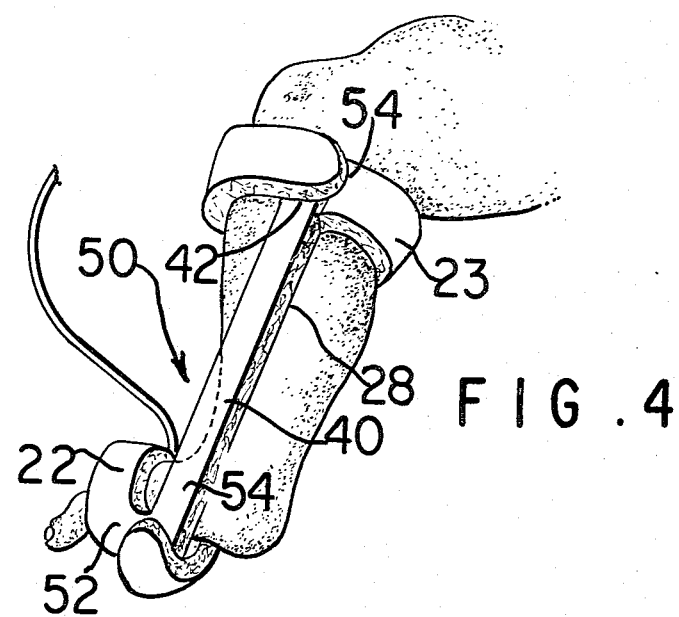
FIG. 4 illustrates one method of affixing the embodiment of FIG. 3 to an infant's foot and lower leg for securing these against motion while fluids are infused in the infant's leg.

FIG. 4 shows one method of applying the embodiment of FIG. 3 to the foot and lower leg of an infant for securing this extremity against movement while fluids are being infused in the veins of the foot or leg. Side 38 of second portion 32 is placed against the inner side of the infant's leg and ankle. First strap 22 is wrapped around the top of the foot and over the instep and then it is affixed to second outer side 40 by fabric hook 42 on or adjacent curved connecting section 52. Strap 23 is wound around the leg just above the calf area and is affixed to outer side 40 on or adjacent connecting section 54 of first portion 28 on the side thereof opposite curved connecting section 52 by its fabric hook 42.

Because the straps 22 and 23 are flexible and thus adapted for application to extremities disposed at various angles thereto, either the embodiment of FIG. 2 or that of FIG. 3 can be used to secure the infant's foot and leg against motion. The invention may also be constructed so that one of straps 22 and 23 is transverse to first portion 28 and the other strap is parallel thereto. For application to the infant's foot and leg, the strap parallel to first portion 28 is wound around the toes and affixed to one end of portion 28, while the transverse strap is wound around the calf and affixed to the other end of portion 28.

Accordingly, the present invention provides a relatively more secure means of restraining an infant's extremity against motion while a needle is in place therein for infusion of fluids intravenously. This is achieved without the dangers of taping a securement device directly to the infant's skin. Moreover, the invention is easy to apply and remove, an important clinical advantage.

Although preferred embodiments of the invention have been disclosed for illustrative purposes, it will be appreciated by those skilled in the art that many additions, modifications, and substitutions are possible, without departing from the scope and spirit of the invention as defined in the accompanying claims.

We claim:

1. A support board for use in securing an extremity of an infant against motion while infusing fluids intravenously in said extremity, comprising:
   a rigid support member; and
   means for affixing the support member to the extremity comprising a pad of flexible material shaped to form a plurality of flexible straps for holding the support board to the extremity;
   the pad of flexible material being folded over and overlapping the support member;
   the flexible material being affixed to itself where it overlaps the support member to retain the support member therebetween.

2. The support board of claim 1, wherein the pad of flexible material is folded over and overlaps the support member such that the folded pad is affixed to itself to retain the support member therebetween.

3. The support board of claim 1, wherein at least one strap of the pad is formed transverse to the longitudinal axis of the portion of the pad folded over the support member.

4. The support board of claim 1, wherein at least one strap of the pad is formed parallel to the longitudinal axis of the portion of the pad folded over the support member.

5. The support board of claim 1, wherein the pad comprises a laminate of foam material in contact with the support member and a skin-compatible fabric for contact with the skin of the infant.

6. A method of assembling a support board for use in securing an extremity of an infant against motion while infusing fluids intravenously in said extremity, comprising the steps of:
   providing a rigid support member;
   providing a pad of flexible material having a central member and straps integral with the central member; and
   affixing the central member of the pad to the support member by folding the central member over two sides of the support member such that the folds of the central member overlap the support member; and
   affixing the folds to each other to retain the support member therebetween.

7. A method of securing an extremity of an infant against motion while infusing fluids intravenously in said extremity, comprising the steps of:
   providing a support board having a rigid support member and a pad of flexible cushioning material affixed to the support member and shaped to form a plurality of flexible straps each having a free end;
   placing the infant's extremity on the pad of flexible cushioning material affixed to the rigid support member;
   wrapping the flexible straps around the extremity and affixing the free end of each strap to the support board to hold the extremity thereto;
   affixing the support board to a stationary object; and
   infusing fluids intravenously in the infant's extremity while it is thus secured against motion.

* * * * *